US00PP24520P2

(12) United States Plant Patent
Akai

(10) Patent No.: US PP24,520 P2
(45) Date of Patent: Jun. 3, 2014

(54) ***PETUNIA* PLANT NAMED 'SUNDASIRO'**

(50) Latin Name: *Petunia×hybrida*
Varietal Denomination: Sundasiro

(75) Inventor: Nobutaka Akai, Miyazaki (JP)

(73) Assignee: Suntory Flowers Limited, Tokyo (JP)

( * ) Notice: Subject to any disclaimer, the term of this patent is extended or adjusted under 35 U.S.C. 154(b) by 160 days.

(21) Appl. No.: 13/506,501

(22) Filed: Apr. 23, 2012

(51) Int. Cl.
*A01H 5/00* (2006.01)

(52) U.S. Cl.
USPC ..... Plt./356.12

(58) Field of Classification Search
USPC ..... Plt./356.12, 356.15
See application file for complete search history.

*Primary Examiner* — June Hwu
(74) *Attorney, Agent, or Firm* — C. A. Whealy

(57) ABSTRACT

A new and distinct cultivar of *Petunia* plant named 'Sundasiro', characterized by its semi-upright and mounding plant habit; vigorous growth habit; freely branching habit; early and freely flowering habit; long flowering period; double-type white-colored flowers; and good garden performance.

1 Drawing Sheet

Botanical designation: *Petunia×hybrida.*
Cultivar denomination: 'SUNDASIRO'.

CROSS-REFERENCED TO RELATED APPLICATIONS

Title: *Petunia* Plant Named 'SUNDAPIN'.
Applicant: Nobutaka AKAI.
Filed: Concurrently with this application (U.S. Plant patent application Ser. No. 13/506,499).

BACKGROUND OF THE INVENTION

The present invention relates to a new and distinct cultivar of *Petunia* plant, botanically known as *Petunia×hybrida* and hereinafter referred to by the name 'Sundasiro'.

The new *Petunia* plant is a product of a planned breeding program conducted by the Inventor in Miyazaki-shi, Miyazaki, Japan. The objective of the breeding program is to create new semi-upright and mounding *Petunia* plants with attractive double-type flowers.

The new *Petunia* plant is a naturally-occurring branch mutation of a proprietary selection of *Petunia×hybrida* identified as code name AK-Pet3, not patented. The new *Petunia* plant was discovered and selected by the Inventor on a single flowering plant from within a population of plants of the mutation parent selection in a controlled greenhouse environment in Miyazaki-shi, Miyazaki, Japan in June, 2010.

Asexual reproduction of the new *Petunia* plant by terminal cuttings in a controlled environment in Miyazaki-shi, Miyazaki, Japan since June, 2010 has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sundasiro'. These characteristics in combination distinguish 'Sundasiro' as a new and distinct *Petunia* plant:

1. Semi-upright and mounding plant habit.
2. Vigorous growth habit.
3. Freely branching habit.
4. Early and freely flowering habit.
5. Long flowering period.
6. Double-type white-colored flowers.
7. Good garden performance.

Plants of the new *Petunia* can be compared to plants of the mutation parent selection. Plants of the new *Petunia* differ primarily from plants of the mutation parent selection in flower color as plants of the mutation parent selection have bright red purple-colored flowers. In addition, plants of the new *Petunia* have darker green-colored leaves than plants of the mutation parent selection.

Plants of the new *Petunia* can be compared to plants of the *Petunia* 'Sundapin', disclosed in a U.S. Plant Patent application filed concurrently. Plants of the new *Petunia* differ primarily from plants of 'Sundapin' in flower color as plants of 'Sundapin' have light red purple-colored flowers.

Plants of the new *Petunia* can also be compared to plants of the *Petunia* 'AK101', disclosed in U.S. Plant Pat. No. 21,951. In side-by-side comparisons conducted in Higashiomi, Shiga, Japan, plants of the new *Petunia* and 'AK101' differed primarily in the following characteristics:

1. Plants of the new *Petunia* were more upright and mounding than and not as trailing as plants of 'AK101'.
2. Plants of the new *Petunia* had shorter lateral branches than plants of 'AK101'.
3. Plants of the new *Petunia* had shorter leaves than plants of 'AK101'.
4. Flowers of plants of the new *Petunia* were larger and had fewer petals than flowers of plants of 'AK101'.
5. Plants of the new *Petunia* and 'AK101' differed in flower color as plants of 'AK101' had red purple-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sundasiro' grown in a container.

The photograph at the bottom of the sheet is a close-up view of a typical flowering plant of 'Sundasiro'.

DETAILED BOTANICAL DESCRIPTION

The aforementioned photographs and following observations, measurements and values describe plants grown during the autumn in 15-cm containers in an outdoor nursery in Higashiomi, Shiga, Japan and under cultural practices typical of commercial production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Petunia×hybrida* 'Sundasiro'.

Parentage: Naturally-occurring branch mutation of a proprietary selection of *Petunia×hybrida* identified as code name AK-Pet3, not patented.

Propagation:

*Type.*—By terminal cuttings.

*Time to initiate roots, summer.*—About eight days at temperatures of 30° C. to 35° C.

*Time to initiate roots, winter.*—About twelve days at temperatures of 20° C. to 22° C.

*Time to produce a rooted young plant, summer.*—About 15 days at temperatures of 30° C. to 35° C.

*Time to produce a rooted young plant, winter.*—About 20 days at temperatures of 20° C. to 22° C.

*Root description.*—Fibrous; white in color.

*Rooting habit.*—Freely branching.

Plant description:

*Plant and growth habit.*—Semi-upright and mounding plant habit; freely branching habit with numerous lateral branches developing per plant; pinching enhances lateral branch development; vigorous growth habit.

*Plant height.*—About 20.6 cm.

*Plant diameter.*—About 41 cm.

Lateral branch description:

*Length.*—About 19.9 cm.

*Diameter.*—About 1.9 mm.

*Internode length.*—About 1.5 cm.

*Strength.*—Strong, flexible.

*Aspect.*—Upright to somewhat outwardly.

*Texture.*—Densely pubescent.

*Color.*—Close to 143B.

Foliage description:

*Arrangement.*—Alternate, simple.

*Length.*—About 3.6 cm.

*Width.*—About 2.1 cm.

*Shape.*—Ovate.

*Apex.*—Broadly acute.

*Base.*—Obtuse.

*Margin.*—Entire; undulate.

*Texture, upper and lower surfaces.*—Densely pubescent.

*Venation pattern.*—Pinnate; reticulate.

*Color.*—Developing leaves, upper surface: Close to 138A. Developing leaves, lower surface: Close to 138B. Fully expanded leaves, upper surface: Close to 137B; venation, close to 144A. Fully expanded leaves, lower surface: Close to 138A; venation, close to 146D.

*Petioles.*—Length: About 2.8 mm. Diameter: About 2.3 mm. Texture, upper and lower surfaces: Pubescent. Color, upper and lower surfaces: Close to 144A.

Flower description:

*Flower arrangement and habit.*—Double-type flowers arising from upper leaf axils; freely flowering habit with usually about 18 flowers developing per plant; flowers face upright to outwardly.

*Fragrance.*—None detected.

*Natural flowering season.*—Early flowering habit, plants of the new *Petunia* initiate and develop flowers about three to four weeks after planting; long flowering period; flowering commences naturally during the spring and plants flower continuously throughout the summer until late autumn in Japan.

*Flower longevity.*—Individual flowers last about seven to ten days on the plant; flowers persistent.

*Flower diameter.*—About 4.5 cm.

*Flower length (depth).*—About 3.9 cm.

*Throat diameter.*—About 1.5 cm.

*Tube diameter, base.*—About 4.2 mm.

*Tube length.*—About 2.3 cm.

*Flower buds.*—Shape: Obconical; apex, twisting. Length: About 2.8 cm. Diameter: About 1.1 cm. Color: Close to 1C.

*Corolla.*—Arrangement: About 17 petals fused at the base. Petal length from throat: About 1.4 cm. Petal width: About 1.8 cm. Petal shape: Spatulate. Petal apex: Mucronate. Petal margin: Entire; weakly undulate. Petal texture, upper and lower surfaces: Smooth, glabrous. Throat texture: Smooth, glabrous. Tube texture: Pubescent. Color: Petal, when opening and fully opened, upper surface: Close to NN155C; venation, close to NN155C; color does not change with development. Petal, when opening and fully opened, lower surface: Close to NN155B; venation, close to 143A. Throat: Close to 157C. Tube: Close to N144C.

*Calyx.*—Arrangement: One star-shaped calyx tube with five sepals fused at the base per flower. Sepal length: About 1.6 cm. Sepal width: About 4.1 mm. Sepal shape: Narrowly elliptic. Sepal apex: Obtuse. Sepal margin: Entire. Sepal texture, upper and lower surfaces: Pubescent. Color: Developing and fully developed sepals, upper surface: Close to 143A. Developing and fully developed sepals, lower surface: Close to 143B.

*Peduncles.*—Length: About 2.2 cm. Diameter: About 1.2 mm. Strength: Strong. Texture: Densely pubescent. Color: Close to 143B.

*Reproductive organs.*—Stamens: Quantity per flower: About three. Stamen length: About 7.6 mm to 12.7 mm. Anther shape: Ellipsoidal. Anther size: About 1.7 mm by 2.4 mm. Anther color: Close to 8D. Pollen amount: Scarce. Pollen color: Close to 8D. Pistils: Quantity per flower: One. Pistil length: About 7 mm. Style color: Close to 144D. Stigma shape: Transversely ellipsoidal. Stigma color: Close to 144B. Ovary color: Close to 144B. Seeds and fruits: Seed and fruit development have not been observed on plants of the new *Petunia*.

Garden performance: Plants of the new *Petunia* have been observed to have good garden performance and to tolerate rain, wind and temperatures ranging from about −5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sundasiro' as illustrated and described.

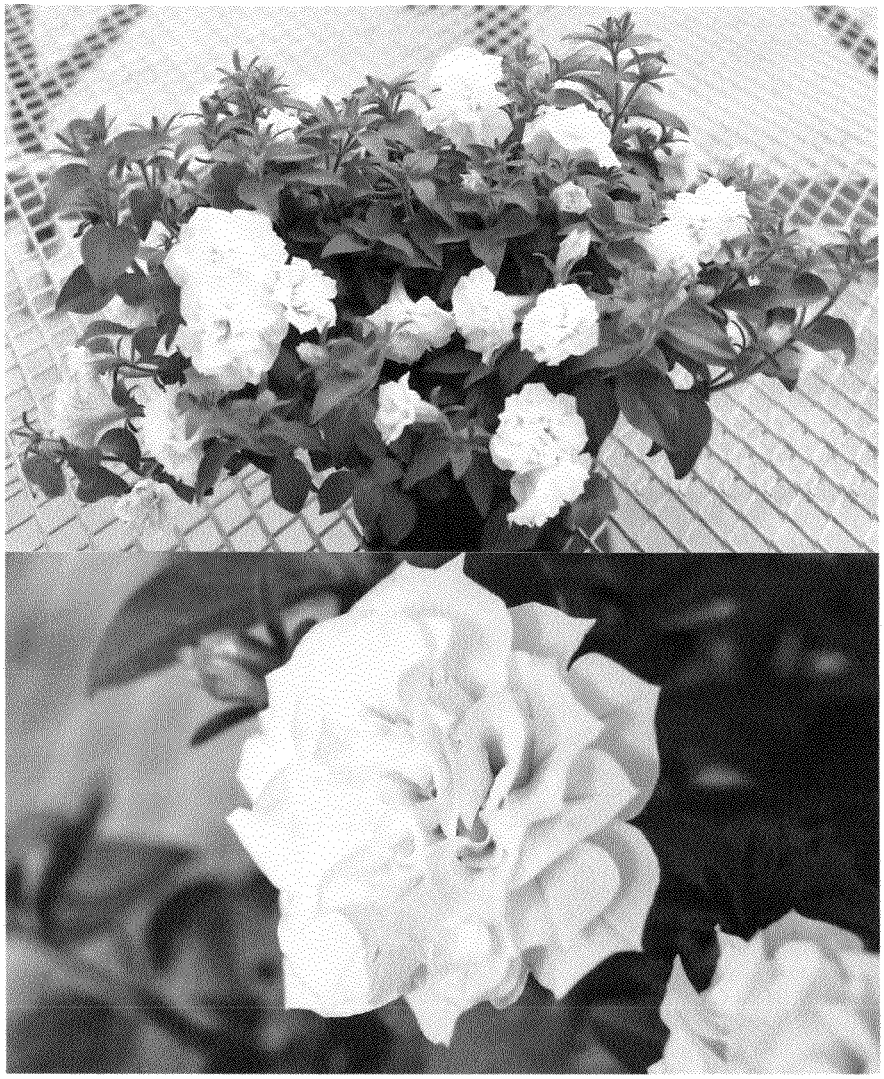

* * * * *